(12) United States Patent　　(10) Patent No.: US 9,005,155 B2
Sugimoto　　(45) Date of Patent: Apr. 14, 2015

(54) DEVICES AND METHODS FOR TREATING HEART FAILURE

(71) Applicant: Hiroatsu Sugimoto, Cambridge, MA (US)

(72) Inventor: Hiroatsu Sugimoto, Cambridge, MA (US)

(73) Assignee: DC Devices, Inc., Tewksbury, MA (US)

( * ) Notice: Subject to any disclaimer, the term of this patent is extended or adjusted under 35 U.S.C. 154(b) by 172 days.

(21) Appl. No.: 13/757,839

(22) Filed: Feb. 3, 2013

(65) Prior Publication Data

US 2013/0204175 A1　　Aug. 8, 2013

Related U.S. Application Data

(60) Provisional application No. 61/595,010, filed on Feb. 3, 2012.

(51) Int. Cl.
*A61M 27/00* (2006.01)
*A61F 2/24* (2006.01)

(52) U.S. Cl.
CPC ............ *A61M 27/002* (2013.01); *A61F 2/2493* (2013.01)

(58) Field of Classification Search
CPC ....................................... A61B 17/0057; A61B 2017/00575–2017/00632; A61M 27/00–27/002
USPC ............................ 604/8–9; 623/1.26; 606/213
See application file for complete search history.

(56) References Cited

U.S. PATENT DOCUMENTS

| 4,018,228 A | 4/1977 | Goosen |
| 4,705,507 A | 11/1987 | Boyles |
| 5,108,420 A | 4/1992 | Marks |
| 5,171,233 A | 12/1992 | Amplatz et al. |
| 5,334,217 A | 8/1994 | Das |
| 5,429,144 A | 7/1995 | Wilk |
| 5,578,045 A | 11/1996 | Das |
| 5,693,090 A | 12/1997 | Unsworth et al. |
| 5,702,412 A | 12/1997 | Popov et al. |
| 5,725,552 A | 3/1998 | Kotula et al. |

(Continued)

FOREIGN PATENT DOCUMENTS

| EP | 1470785 | 10/2004 |
| EP | 2537490 | 12/2012 |

(Continued)

OTHER PUBLICATIONS

Ad et al., "A one way valved atrial septal patch: A new surgical technique and its clinical application", The Journal of Thoracic and Cardiovascular Surgery, vol. 111, Apr. 1996, pp. 841-848.

(Continued)

*Primary Examiner* — Philip R Wiest
*Assistant Examiner* — Benjamin Klein
(74) *Attorney, Agent, or Firm* — Liu Law Office; Helen S. Liu

(57) ABSTRACT

The present teachings provide a device and method of making and using thereof. Specifically, one aspect of the present teachings provides a device comprising a shunt having a distal end and a proximal end and the shunt positionable across the septum of a heart. Certain embodiments of the present teachings also include a distal anchoring portion connecting to the distal end of the shunt portion and a proximal anchoring portion connecting to the proximal end of the shunt portion. Another aspect of the present teachings provide methods of using thereof to modify the pressure difference in a heart chamber.

19 Claims, 6 Drawing Sheets

(56) References Cited

U.S. PATENT DOCUMENTS

| | | |
|---|---|---|
| 5,824,071 A | 10/1998 | Nelson et al. |
| 5,876,436 A | 3/1999 | Vanney et al. |
| 6,050,936 A | 4/2000 | Schweich et al. |
| 6,077,281 A | 6/2000 | Das |
| 6,123,715 A | 9/2000 | Amplatz |
| 6,156,055 A | 12/2000 | Ravenscroft |
| 6,190,353 B1 | 2/2001 | Makower et al. |
| 6,193,734 B1 | 2/2001 | Bolduc et al. |
| 6,258,119 B1 | 7/2001 | Hussein et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,383,195 B1 | 5/2002 | Richard |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,303 B1 | 10/2002 | Amplatz et al. |
| 6,527,746 B1 | 3/2003 | Oslund et al. |
| 6,626,936 B2 | 9/2003 | Stinson |
| 6,641,610 B2 | 11/2003 | Wolf et al. |
| 6,645,143 B2 | 11/2003 | Van Tassel et al. |
| 6,666,885 B2 | 12/2003 | Moe |
| 6,712,836 B1 | 3/2004 | Berg et al. |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,936,058 B2 | 8/2005 | Forde et al. |
| 6,979,343 B2 | 12/2005 | Russo et al. |
| 7,001,409 B2 | 2/2006 | Amplatz et al. |
| 7,097,653 B2 | 8/2006 | Freudenthal et al. |
| 7,105,024 B2 | 9/2006 | Richelsoph |
| 7,159,593 B2 | 1/2007 | McCarthy et al. |
| 7,226,466 B2 | 6/2007 | Opolski |
| 7,317,951 B2 | 1/2008 | Schneider et al. |
| 7,338,514 B2 | 3/2008 | Wahr et al. |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,524,330 B2 | 4/2009 | Berreklouw |
| 7,530,995 B2 | 5/2009 | Quijano et al. |
| 7,625,392 B2 | 12/2009 | Coleman et al. |
| 7,658,747 B2 | 2/2010 | Forde et al. |
| 7,699,297 B2 | 4/2010 | Cicenas et al. |
| 7,766,966 B2 | 8/2010 | Richelsoph |
| 7,819,890 B2 | 10/2010 | Russo et al. |
| 7,842,026 B2 | 11/2010 | Cahill et al. |
| 7,871,419 B2 | 1/2011 | Devellian et al. |
| 7,927,370 B2 | 4/2011 | Webler et al. |
| 7,976,564 B2 | 7/2011 | Blaeser et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,070,708 B2 | 12/2011 | Rottenberg et al. |
| 8,091,556 B2 | 1/2012 | Keren et al. |
| 8,157,860 B2 | 4/2012 | McNamara et al. |
| 8,172,896 B2 | 5/2012 | McNamara et al. |
| 8,252,042 B2 | 8/2012 | McNamara et al. |
| 8,460,372 B2 | 6/2013 | McNamara et al. |
| 2001/0029368 A1 | 10/2001 | Berube |
| 2002/0029061 A1 | 3/2002 | Amplatz et al. |
| 2002/0062135 A1 | 5/2002 | Mazzocchi et al. |
| 2002/0072765 A1 | 6/2002 | Mazzocchi et al. |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0095173 A1 | 7/2002 | Mazzocchi et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2002/0198563 A1 | 12/2002 | Gainor et al. |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0111095 A1 | 6/2004 | Gordon et al. |
| 2004/0133236 A1 | 7/2004 | Chanduszko et al. |
| 2004/0143292 A1 | 7/2004 | Marino |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | McCarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0049692 A1 | 3/2005 | Numamolo et al. |
| 2005/0065548 A1 | 3/2005 | Marino et al. |
| 2005/0065589 A1 | 3/2005 | Schneider et al. |
| 2005/0070934 A1 | 3/2005 | Tanaka et al. |
| 2005/0075655 A1 | 4/2005 | Bumbalough et al. |
| 2005/0080400 A1 | 4/2005 | Corcoran et al. |
| 2005/0148925 A1 | 7/2005 | Rottenberg et al. |
| 2005/0165344 A1 | 7/2005 | Dobak |
| 2005/0187616 A1 | 8/2005 | Realyvasquez |
| 2005/0240205 A1 | 10/2005 | Berg et al. |
| 2005/0267523 A1 | 12/2005 | Devellian et al. |
| 2005/0273075 A1 | 12/2005 | Kulevitch et al. |
| 2005/0288722 A1 | 12/2005 | Eigler et al. |
| 2006/0004434 A1 | 1/2006 | Forde et al. |
| 2006/0009715 A1 | 1/2006 | Khairkhahan et al. |
| 2006/0009800 A1 | 1/2006 | Christianson et al. |
| 2006/0122646 A1 | 6/2006 | Corcoran et al. |
| 2006/0122647 A1 | 6/2006 | Callaghan et al. |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0241745 A1 | 10/2006 | Solem |
| 2006/0253184 A1 | 11/2006 | Amplatz et al. |
| 2006/0276882 A1 | 12/2006 | Case et al. |
| 2007/0016250 A1 | 1/2007 | Blaeser et al. |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0168019 A1 | 7/2007 | Amplatz et al. |
| 2007/0185513 A1 | 8/2007 | Woolfson et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154302 A1 | 6/2008 | Opolski et al. |
| 2008/0154351 A1 | 6/2008 | Leewood et al. |
| 2008/0172123 A1 | 7/2008 | Yadin |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249612 A1 | 10/2008 | Osborne et al. |

(56) References Cited

U.S. PATENT DOCUMENTS

| | | |
|---|---|---|
| 2008/0262592 A1 | 10/2008 | Jordan et al. |
| 2008/0312679 A1 | 12/2008 | Hardert et al. |
| 2009/0018562 A1 | 1/2009 | Amplatz et al. |
| 2009/0025820 A1 | 1/2009 | Adams |
| 2009/0030495 A1 | 1/2009 | Koch |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Faman et al. |
| 2009/0112244 A1 | 4/2009 | Freudenthal |
| 2009/0131978 A1 | 5/2009 | Gainor et al. |
| 2009/0171386 A1 | 7/2009 | Amplatz et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030321 A1 | 2/2010 | Mach |
| 2010/0049307 A1 | 2/2010 | Ren |
| 2010/0057192 A1 | 3/2010 | Celermajer |
| 2010/0063578 A1 | 3/2010 | Ren et al. |
| 2010/0094335 A1 | 4/2010 | Gerberging et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249909 A1 | 9/2010 | McNamara et al. |
| 2010/0249910 A1* | 9/2010 | McNamara et al. ......... 623/1.26 |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg |
| 2011/0257723 A1 | 10/2011 | McNamara et al. |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | McNamara et al. |
| 2012/0130301 A1 | 5/2012 | McNamara et al. |
| 2012/0165928 A1 | 6/2012 | Nitzan et al. |
| 2012/0259263 A1 | 10/2012 | Celermajer et al. |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0231737 A1 | 9/2013 | McNamara et al. |
| 2013/0267885 A1 | 10/2013 | Celermajer et al. |

FOREIGN PATENT DOCUMENTS

| | | |
|---|---|---|
| WO | 9527448 | 10/1995 |
| WO | 2008058940 | 5/2008 |
| WO | 2010111666 | 9/2010 |
| WO | 2014150106 | 9/2013 |

OTHER PUBLICATIONS

Althoff et al., "Long-Term Follow up of a Fenestrated Amplatzer Atrial Septal Occluder in Pulmonary Arterial Hypertension," Chest 2008, 133:183-85, 5 pages.

Atz et al., "Preoperative Management of Pulmonary Venous Hypertension in Hypoplastic Left Heart Syndrome With Restrictive Atrial Septal Defect". The American Journal of Cardiology, vol. 83. Apr. 15, 1999, pp. 1224-1228.

Bailey, "Nanotechnology in Prosthetic Heart Valves," approx. date 2005, presentation, 31 pages.

Bolling, "Direct Flow Medical-My Valve is Better," Apr. 23, 2009, presentation. 21 pages.

Cheatham, John P., "Intervention in the critically ill neonate and infant with hypoplastic left heart syndrome and intact atrial septum", Journal of Interventional Cardiology, vol. 14, No. 3, 2001, pp. 357-366.

Coselli, Joseph S., "No! valve replacement: patient prosthetic mismatch rarely occurs," Texas Heart Insitute, Apr. 25, 2009, 75 pages.

Design News, "Low Power Piezo Motion". http://www.designnews.com/document.asp?doc—id=229053&dfpPParams &dfpPParams=ht—13,aid—229053&dfpLayout=article, May 14, 2010, 3 pages.

European Application Serial No. EP10772411.4, European Search Opinion and Supplementary European Search Report mailed Mar. 16, 2012, 5 pages.

European Application Serial No. EP12180631.9, European Search Report mailed Nov. 19, 2012, 5 pages.

Gaudiani et al., "A Philosophical Approach to Mitral Valve Repair," Apr. 24, 2009, presentation. 28 pages.

Hijazi, "Valve Implantation: Ziyad M. Hijazi," May 10, 2007, presentation, 36 pages.

International Application Serial No. PCT/AU2007/001704, International Preliminary Report Patentability, mailed Aug. 22, 2008, 5 pages.

International Application Serial No. PCT/AU2007/001704, International Search Report, mailed Jan. 16, 2008, 4 pages.

International Application Serial No. PCT/AU2007/001704, Written Opinion, mailed Jan. 15. 2008, 5 pages.

International Application Serial No. PCT/US2010/026574, International Preliminary Report on Patentability, mailed Nov. 10, 2011, 6 pages.

International Application Serial No. PCT/US2010/026574, International Search Report, mailed Nov. 19, 2010, 5 pages.

International Application Serial No. PCT/US2010/058110, International Preliminary Report on Patentability, mailed Nov. 27, 2012, 7 pages.

International Application Serial No. PCT/US2010/058110, International Search Report and Written Opinion, mailed Aug. 26, 2011, 12 pages.

International Application Serial No. PCT/US2011/022895 International Search Report & Written Opinion, mailed Oct. 24, 2011, 10 pages.

International Application Serial No. PCT/US2011/041841, International Preliminary Report on Patentability and Written Opinion, mailed Jun. 6, 2013, 7 pages.

International Application Serial No. PCT/US2011/041841, International Search Report and Written Opinion, mailed Feb. 9. 2012, 10 pages.

International Application Serial No. PCT/US2012/024680. International Preliminary Report on Patentability and Written Opinion, mailed Aug. 22, 2013, 6 pages.

(56) References Cited

OTHER PUBLICATIONS

International Application Serial No. PCT/US2012/024680, International Search Report and Written Opinion, mailed Oct. 23, 2012, 10 pages.
International Application Serial No. PCT/US2012/071588, International Search Report and Written Opinion, mailed Apr. 19, 2013, DC Devices, Inc., 17 pages.
Larios et al., "The Use of an Artificial Foraminal Valve Prosthesis in the Closure of Interatrial and Interventricular Septal Defects." Dis. Chest. 1959: 36; 631-41, 11 pages.
Leon, "Transcatheter Aortic Valve Therapy: Summary Thoughts," Jun. 24, 2009, presentation, 19 pages.
Merchant et al., "Advances in Arrhythmia and Electrophysiology, Implantable Sensors for Heart Failure", Circ. Arrhythm. Electrophysiol., vol. 3, Dec. 2010, pp. 657-667.
Moses, "The Good, the Bad and the Ugly of Transcatheter AVR," Jul. 10, 2009, presentation, 28 pages.
O'Loughlin et al., "Insertion of a Fenestrated Amplatzer Atrial Sestosotomy Device for Severe Pulmonary Hypertension," Heart Lung Circ. 2006, 15(4):275-77, 3 pages.
Park et al., "Blade atrial septostomy: collaborative study", Circulation, Journal of the American Heart Association, vol. 66, No. 2, Aug. 1982, pp. 258-266.
Pedra et al., "Stent Implantation to Create Interatrial Communications in Patients With Complex Congenital Heart Disease", Catheterization and Cardiovascular interventions 47, Jan. 27, 1999, pp. 310-313.
Perry et al., "Creation and Maintenance of an Adequate Interatrial Communicationin left Atrioventricular Valve Atresia or Stenosis", The American Journal of Cardiology, vol. 58, Sep. 15, 1986, pp. 622-626.
Philips et al., "Ventriculofemoroatrial shunt: a viable alternative for the treatment of hydrocephalus", J. Neurosurg., vol. 86, Jun. 1997, pp. 1063-1066.
Sommer et al., "Transcatheter Creation of Atrial Septal Defect and Fontan Fenestration with "Butterfly" Stent Technique", Supplement to Journal of the American College of Cardiology, vol. 33, No. 2, Supplement A, Feb. 1999, 3 pages.
Stone, "Transcatheter Devices for Mitral Valve Repair, Surveying the Landscape," Jul. 10, 2009, presentation. 48 pages.
Stormer et al., "Comparative Study of in vitro Flow Characteristics between a Human Aortic Valve and a Designed Aortic Valve and Six Corresponding Types of Prosthetic Heart Valves," Eur. Surg. Res. 8: 117-131 (1976), 15 pages.
Watterson et al., "Very Small Pulmonary Arteries Central End-to-Side Shunt", Ann. Thorac. Surg., vol. 52, No. 5, Nov. 1991, pp. 1132-1137.

\* cited by examiner

DEVICES AND METHODS FOR TREATING HEART FAILURE

CROSS REFERENCE TO RELATED APPLICATIONS

This application claims priority to and the benefit of U.S. Provisional Patent Application Ser. No. 61/595,010, entitled "DEVICES AND METHODS FOR TREATING HEART FAILURE," filed on Feb. 3, 2012, the entirety of which is incorporated herein by reference.

FIELD

The present teachings relate to devices and methods of use thereof for treating heart failure. An aspect of the present teachings relates to a device that can be used to change (e.g., reduce) the blood pressure in a heart chamber, for example, by creating a shunt and optionally regulating the flow of blood through the shunt in order to enhance the therapeutic effect of the shunt. The present teachings further relate to a method of utilizing such a device, for example, in treating congestive heart failure related conditions, for example, acute cardiogenic pulmonary edema caused by an elevated pressure in a left side chamber in the heart.

BACKGROUND

Congestive heart failure (CHF) is a condition that affects millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes a reduced cardiac output and inadequate blood to meet the needs of body tissues.

Treatments for CHF include: (1) pharmacological treatments, (2) assisting systems, and (3) surgical treatments. Pharmacological treatments, e.g., with diuretics, are used to reduce the workload of a heart by reducing blood volume and preload. While pharmacological treatments can improve quality of life, they have little effect on survival. Assisting devices, e.g., mechanical pumps, are used to reduce the load on a heart by performing all or part of the pumping function normally done by the heart. However, in a chronic ischemic heart, high-rate pacing may lead to an increased diastolic pressure, calcium overload, and damages to the muscle fibers. There are at least three surgical procedures for treating a heart failure: (1) heart transplant, (2) dynamic cardiomyoplasty, and (3) the Batista partial left ventriculectomy. These surgical treatments are invasive and have many limitations.

CHF is generally classified into systolic heart failures (SHF) or diastolic heart failures (DHF). In a SHF, the pumping action of a heart is reduced or weakened. A normal ejection fraction (EF), the volume of blood ejected out of the left ventricle (stroke volume) divided by the maximum volume remaining in the left ventricle at the end of the diastole or relaxation phase, is greater than 50%. In a systolic heart failure, EF is decreased to less than 50%. A patient with SHF may have an enlarged left ventricle because of cardiac remodeling developed to maintain an adequate stroke-volume. This pathophysiological phenomenon is often associated with an increased atrial pressure and an increased left ventricular filling pressure.

DHF is a heart failure without any major valve disease every though the systolic function of the left ventricle is preserved. Generally, DHF is a failure of the ventricle to adequately relax and expand, resulting in a decrease in the stroke volume of the heart. Presently, there are very few treatment options for patients suffering from DHF. DHF afflicts between 30% and 70% of patients with CHF.

There are several known techniques that can be used to treat the symptoms of DHF. Without attempting to characterize the following references, for example, U.S. Pat. No. 8,091,556 by Keren et al. discloses the use of an interatrial pressure relief shunt with a valve and a tissue affixation element at each end of the shunt; and United States Patent Application Publication No. 20050165344 by Dobak discloses a pressure relief system with an interatrial septal conduit with an emboli barrier or trap mechanism to prevent cryptogenic stroke due to thrombi or emboli crossing the conduit into the left sided circulation. Dobak also discloses a conduit with a one-way valve which directs blood flow from the left atrium to the right atrium.

The constantly evolving nature of heart failures represents a significant challenge for the treatment. Therefore, there is a need for novel and adaptable methods and devices for treating DHF, for example, by creating a pressure relief shunt which can be retrieved, repositioned, adjusted, expanded, contracted, occluded, sealed and/or otherwise altered as required to treat a patient. Furthermore, there exists a need for treating DHF with devices and methods that can self-adjust over time either in accordance with or in anticipation of the gradual hemodynamic changes associated with a heart failure.

SUMMARY

An aspect of the present teachings provides devices for regulating the blood pressure in a heart chamber. In various embodiments, each of the devices comprises a shunt positionable across a septum of a heart, including, in the fossa ovalis. In some embodiments, the shunt enables blood flow between a left heart chamber and a right heart chamber. In certain embodiments, the flow rate of the device is a function of the pressure in a left heart chamber. In particular embodiments, the flow rate of the device is a function of the pressure difference between a left heart chamber and a right heart chamber.

Another aspect of the present teachings provides methods of making and using a device of the present teachings to regulate the blood pressure in a heart chamber.

One embodiment of the present teachings provides an implantable medical device comprising a shunt portion with a distal end, a proximal end, a distal anchoring portion connecting to the distal end of the shunt portion, and a proximal anchoring portion connecting to the proximal end of the shunt portion, wherein the shunt portion has a generally tubular profile with a mesh-like structure that allows a first amount of blood to communicate from a first heart chamber to a second heart chamber.

One embodiment of the present teachings provides an implantable medical device comprising a shunt portion with a distal end, to proximal end, a central lumen, a distal anchoring portion connecting to the distal end of the shunt portion, and as proximal anchoring portion connecting to the proximal end of the shunt portion, wherein the device has a first elongated delivery profile, and a second generally hairpin or U-shaped profile.

One embodiment of the present teachings provides an implantable medical device comprising a shunt portion with a distal end, to proximal end, a central lumen, a distal anchoring portion connecting, to the distal end of the shunt portion, and a proximal anchoring portion connecting to the proximal end of the shunt portion, wherein the distal anchoring portion, the shunt portion, and the proximal anchoring portion are aligned axially to form as first elongated profile, wherein the distal anchoring portion and the proximal anchoring portion bend toward a same direction away from the central lumen of the shunt portion forming as second hairpin shaped profile.

Another aspect of the present teachings provides a delivery assembly for percutaneously delivering an implantable device. In various embodiments, the implantable device is used to regulate the pressure differential between two chambers of the heart. In various embodiments, a delivery assembly comprises a delivery sheath with a distal portion and a lumen, an implantable device as described herein having a first elongated profile and a second hairpin or U-shaped profile, wherein the device, in its first elongated profile, is slidably disposed inside the lumen of the distal portion of the delivery sheath, a delivery catheter with a distal end, wherein the delivery catheter is slidably positioned within the lumen of the delivery sheath, and wherein the distal end of the delivery catheter engages the proximal end of the device.

Another aspect of the present teachings provides a method of implanting a pressure regulating device between two chambers of the heart. In various embodiments, the method comprises providing a delivery assembly of the present teachings, advancing the delivery assembly through an aperture, exposing the distal half of a device as described herein, retracting the delivery assembly proximally so that a distal anchoring portion of the device contacts a septum, exposing the proximal half of the device, disengaging a delivery catheter of the present teachings from the device, and retracting the delivery sheath and the delivery catheter from the body.

DETAILED DESCRIPTION

Figure 1:
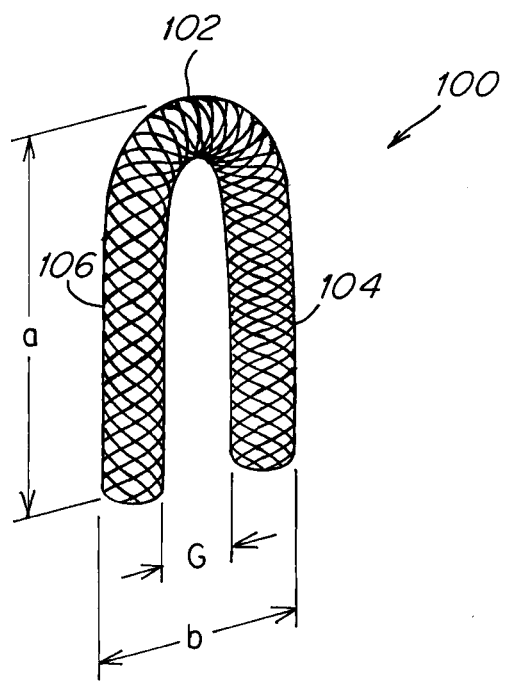
FIG. 1 is a perspective view of an exemplary pressure regulating device in accordance with the present teachings.

The present teachings are described more fully hereinafter with reference to the accompanying drawings, which show certain embodiments of the present teachings. The present teachings may, however, be embodied in many different forms and should not be construed as limited to the embodiments set forth herein. Rather, these embodiments are provided to illustrate various aspects of the present teachings. Like numbers refer to like elements throughout.

The present teachings provide a device and methods of use thereof. For example, the device can be used to regulate the pressure in a heart chamber. Specifically, the device can be used to (a) change an elevated chamber pressure and (b) prevent embolization from the right to left atria in a patient who suffers from CHF or has a Patent Foramen Ovale (PFO) or an Atrial Septal Defect (ASD) but needs a residual flow between the atria so as not to traumatize the heart hemodynamics.

As used herein, the term "proximal" shall mean close to the operator (less into the body) and "distal" shall mean remote from the operator (further into the body). In positioning a medical device from a downstream access point, distal is more upstream and proximal is more downstream.

As explained in further detail below, various embodiments of the present teachings provide medical devices for regulating the pressure in a heart chamber. In some embodiments, a medical device according to the present teachings includes a shunt portion coupled by two anchoring portions. In some embodiments, a medical device is positioned through an aperture in a septum, creating a shunt, for example, between the left and right atria. In some embodiments, the two anchoring portions of the medical device are disposed on the opposite sides of the septum. In some embodiments, a medical device according to the present teachings is extended into an elongated profile for a percutaneous delivery and resume to the preset hairpin-shaped profile in vivo after deployment. As used in this application, unless otherwise indicated, the term "aperture" refers to any anatomical anomalies such as PFO, ASD, VSD, or an anatomical feature created for the purpose of creating a shunt.

The present teachings also disclose a device with a delivery profile and a deployed profile. In various embodiments, the device is elongated in a delivery profile. In various embodiments, the deployed profile is in a general hairpin or U shape. As described in details below, the device can have a straightened, elongated, low-profile delivery configuration suitable for being delivered via a delivery system. The deployed configuration of the device can have a generally U-shaped configuration, radially expanded, and sometimes shortened overall curve length (i.e., the length of an imaginary line tracing from the free end of the proximal anchoring portion, along the proximal anchoring portion, the shunt portion, and the distal anchoring portion, to the free end of the distal anchoring portion). The device can also have two anchoring portions positioned on the opposite sides of the septum, applying a compression force against the septum from both sides, and a shunt portion of the device securely positioned in the aperture.

FIG. 1 shows an exemplary pressure regulating device 100 in its pre-set deployed configuration. The pressure regulating device 100 is in the shape of a hairpin or a "U" with a shunt portion 102 in the middle and a distal anchoring portion 104 and a proximal anchoring portion 106 connected with the shunt portion 102, with both the distal anchoring and proximal anchoring portions, 104 and 106 respectively, extending away from the shunt portion 102 to a direction. As seen in FIG. 1, the distal anchoring portion 104 attaches to the shunt portion 102 at its distal end, and the proximal anchoring portion 106 attaches to the shunt portion 102 at its proximal end. Each of the anchoring portions has a free end and the other end attaching to the shunt portion 102. In this particular embodiment, the entire device 100, including the distal anchoring portion 104, the shunt portion 102, and the proximal anchoring portion 106, has an open mesh-like structure. Additionally, in this particular embodiment, the device 100 has a central lumen extending throughout the entire device 100, from the free end of the proximal anchoring portion 106, through the shunt portion 102, and to the free end of the distal anchoring portion 104. In this particular embodiment, the shunt portion 102 has a generally tubular profile. According to some embodiments, blood from one heart chamber flows through the device 100 reaching another heart chamber. In some embodiments, the pressure inside each heart chamber is altered. According to some embodiments, the blood flows through the mesh opening of the tubular surface of the device 100, through the central lumen, to another chamber of the heart. According to other embodiments, the blood flows from one free end of the device 100, the central lumen, and the other free end of the device 100, thereby being transferred from one heart chamber to another.

Referring to FIG. 1, according to some embodiments, at the device's deployed configuration, the device 100 has a general curved, a hairpin shaped, or a U shaped profile, with the shunt portion 102 in the middle, and the distal anchoring portion 104 and the proximal anchoring portion 106 facing each other. According to some embodiments, the shunt portion 102 is configured to be positioned across an aperture between two heart chambers, the distal anchoring portion 104 attaching to the distal end of the shunt portion 102 and placed at the distal side of the septum between the two heart chambers, and the proximal anchoring portion 106 attaching to the proximal end of the shunt portion 102 and placed at the proximal side of the septum between the two heart chambers. Depending upon the pre-set configuration, both the distal anchoring portion 104 and proximal anchoring portion 106 can bend radially away from the longitudinal axis of the shunt portion 102 and toward each other, with the shunt portion 102 and the non-bending portion of the distal and proximal anchoring portions 104 and 106 of the device 100 remaining a relatively straight profile. In some other embodiments, the deployed shunt portion 102 of the device 100 has a generally curve-shaped or a generally C or U-shaped profile, and both the distal and proximal anchoring portions 104 and 106 have relative straight profiles. According to another embodiment, upon deployment, the shunt portion 102 of the device 100 has as "J" like profile with a curved end and a non-curved end, and one of the distal and proximal anchoring portions 104 and 106 having a relative straight profile attaching to the curved end of the shunt portion 102, and the other anchoring portion having a bent end attaching to the straight end of the shunt portion 102. One skilled in the art would understand that the specific profiles of the shunt portion 102 and the distal and proximal anchoring portions 104 and 106, and the relative positions of the shunt portions and the distal and proximal anchoring portions, 104 and 106, can vary as long as the deployed profile of the device 100 assumes a general "U" shape.

Referring to FIG. 1, according to one embodiment of the present teachings, the device 100 in its deployed profile has an overall length ("a") of 10 mm to 50 mm, an overall width ("b") of 10 mm to 50 mm, and a gap between the free ends of the distal anchoring portion 104 and the proximal anchoring portion 106. In certain embodiments, this gap has a distance "G" which is smaller than the thickness of the septum. In such embodiments, when the device 100 is deployed at a treatment location, the distal anchoring portion 104 and the proximal anchoring portion 106 flex to accommodate the thickness of the septum so that the gap between the free ends of the distal and proximal anchoring portions 104 and 106 expand beyond the pre-set distance "G" to secure the device 100 at the treatment location. In other embodiments, the gap has a distance "G" greater than the thickness of the septum. In such embodiments, when the device 100 is deployed at the treatment location, the general hairpin or U-shape of the deployed device 100 allows the device 100 to be positioned across the aperture while minimizes the contact between the device 100 and the septal tissue. According to yet other embodiments, the gap has a distance "G" that is zero. According to yet other embodiments, the gap has a negative distance where the free end of the distal anchoring portion and the free end of the proximal anchoring portion cross each other at the pre-set deployed configuration. According to various embodiments of the present teachings, the distance "G" ranges from a negative distance to about 50 mm. In particular embodiments, the gap "G" is about 1 mm to about 10 mm.

Figure 2:
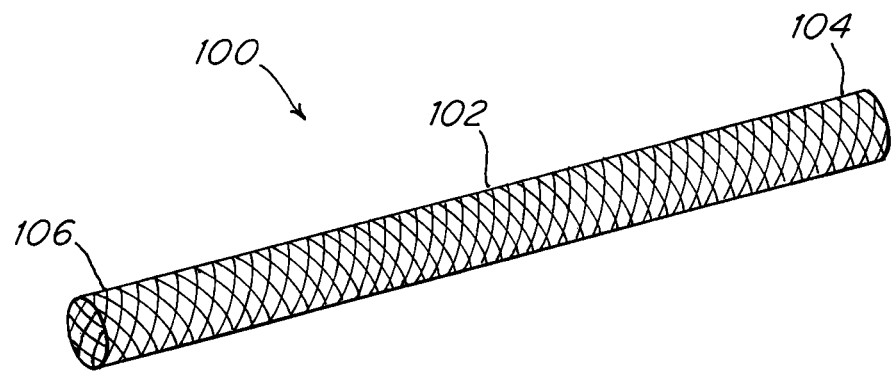
FIG. 2 is a perspective view of the exemplary pressure regulating device of FIG. 1 in a constrained configuration.

Referring to FIG. 2, an exemplary device 100 is shown in its delivery configuration with the distal anchoring portion 104, shunt portion 102, and proximal anchoring portion 106 being aligned axially. One skilled in the art would understand that, according to various embodiments of the present teachings, the straightened delivery profile as illustrated in FIG. 2 exists only when the device 100 is under constraints, such as being inside a delivery catheter/sheath. Thus, what is illustrated in FIG. 2 is not a device 100 in its relaxed state, but in a constrained state. According to various embodiments of the present teachings, in its delivery profile, the entire device 100, including the shunt portion 102 and the distal and proximal anchoring portions 104 and 106, is straightened from its deployed curved shape. Upon deployment, the straightened device 100 resumes its hairpin shaped profile and is positioned through the aperture in a septum with both the distal and proximal anchoring portions, 104 and 106, disposed on the opposite sides of the septum.

According to some embodiments, at least one of the shunt portion 102, the distal anchoring portion 104, and the proximal anchoring portion 106 of the device 100 has a length greater in the delivery profile than in the deployed profile.

Continuing referring to FIGS. 1 and 2, according to various embodiments of the present teachings, the shunt portion 102, the distal anchoring portion 104, and the proximal anchoring portion 106 all have a generally tubular profile with a central lumen extending throughout. In some embodiments, the cross sections of the tubular shunt portion 102 and the tubular anchoring portions 104 and 106 of the device 100 are circular or polygonal, for example, square or hexagonal. According to some embodiments of the present teachings, the cross section of the shunt portion 102 is the same as the cross section of one of the anchoring portions. According to other embodiments of the present teachings, the cross section of the shunt portion 102 has a different shape from the cross section of one of the anchoring portions. According to other embodiments of the present teachings, each of the shunt portion 102, the distal anchoring portion 104, and the proximal anchoring portion 106 has a different cross section profile from another. According to some embodiments of the present teachings, the shunt portion 102, the distal anchoring portion 104, and the proximal anchoring portion 106 have the same cross section. In particular embodiments of the present teachings as illustrate in FIGS. 1 and 2, the cross sections of the shunt portion 102, the distal anchoring portion 104, and the proximal anchoring portion 106 are circular.

Figure 3:
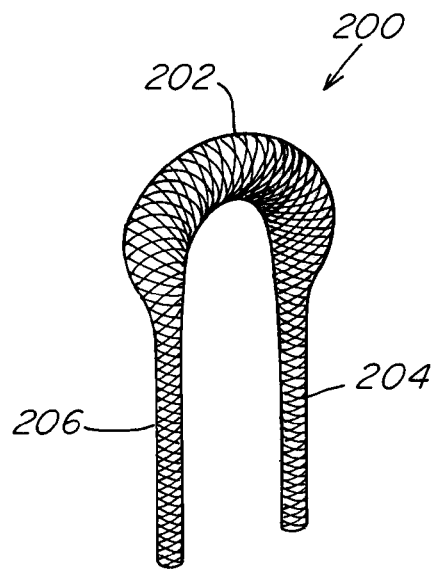
FIG. 3 is a perspective view of an exemplary pressure regulating device in accordance with the present teachings.

Continuing referring to FIGS. 1 and 2, according to various embodiments of the present teachings, in its deployed configuration, the cross sections of the shunt portion 102 and the anchoring portions 104 and 106 of the device 100 are of a same size. According to other embodiments of the present teachings, in its deployed configuration, the cross section of the shunt portion 102 has the same size as the cross section of one of the anchoring portions 104 and 106. According to other embodiments of the present teachings, in its deployed configuration, the cross section of the shunt portion 102 has a different size from the cross section of one of the anchoring portions 104 and 106. According to other embodiments of the present teachings, in its deployed configuration, each of the shunt portion 102, the distal anchoring portion 104, and the proximal anchoring portion 106 has a different size from one another. In some embodiments, the shunt portion 202 of the device 200 has a cross section greater than the distal and proximal anchoring portions, 204 and 206, do, as seen in FIG. 3. In some embodiments of the present teachings, in its deployed configuration, each of the cross sections of the shunt portion 102, the distal anchoring portion 104, and the proximal anchoring portion 106 has a diameter ranging from about 5 mm to about 30 mm. According to one embodiment of the present teachings, in the deployed configuration, each of the cross section area of the shunt portion 102, the distal anchoring portion 104, and the proximal anchoring portion 106 of the device 100 is within the range between about 19 $mm^2$ to about 700 $mm^2$.

In one embodiment of the present teachings, the cross section of the device 100 is reduced for delivery. According to one embodiment of the present teachings, the cross sections of both the shunt portion 102 and the anchoring portions 104 and 106 are reduced as the device 100 is extended into its elongated delivery profile. In another embodiment of the present teachings, the cross section of at least one of the shunt portion 102 and the anchoring portions 104 and 106 is reduced as the device 100 is extended into its elongated delivery profile. According to some embodiments of the present teachings, the cross section of the device 100 in the delivery profile is reduced to about 50% to about 90% of that in its deployed configuration. In some embodiments, the cross section of the device 100 remains the same between the delivery configuration and the deployed configuration.

In various embodiments of the present teachings, the device 100 has a greater length in the delivery configuration than in the deployed configuration. According to some embodiments of the present teachings, both the shunt portion 102 and the anchoring portions 104 and 106 are elongated during the delivery. According to some embodiments of the present teachings, at least one of the shunt portion 102 and the anchoring portions 104 and 106 is elongated during delivery. According to some embodiments of the present teachings, the overall length of the deployed device 100 is between about 30 mm and about 150 mm. According to some embodiments of the present teachings, the straightened length of the device 100, in its delivery profile, is about 20% to about 60% longer than its overall curve length in its deployed profile. In some embodiments, the length of the device 100 in its delivery profile remains the same as in deployed profile.

In some embodiments of the present teachings, the distal anchoring portion 104 and the proximal anchoring portion 106 have a same length. In some embodiments, the distal anchoring portion 104 and the proximal anchoring portion 106 have different lengths. In some embodiments, the distal anchoring portion 104 is longer than the proximal anchoring portion 106. In some other embodiments, the proximal anchoring portion 106 is longer than the distal anchoring portion 104. In some embodiments of the present teachings, each of the distal anchoring portion 104 and proximal anchoring portion 106 of the device 100 has a length between about 10 mm and about 50 mm.

Figure 4:
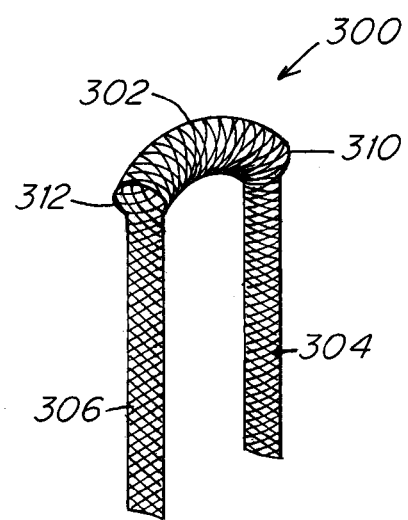
FIG. 4 is a perspective view of an exemplary pressure regulating device in accordance with the present teachings.

In various embodiments of the present teachings, each of the distal and proximal anchoring portions 104 and 106, as shown in FIG. 1, has a generally tubular profile, each with a lumen extending through the entirety of its length. And in some embodiments, the thickness of the tubular surface of the distal and proximal anchoring portions is between about 0.02 mm and about 1 mm. In other embodiments of the present teachings, as shown in FIG. 4, each of the distal and proximal anchoring portions, 304 and 306, has a substantially planar profile. Alternatively, each of the distal and proximal anchoring portions, may also have an elongated curved surface profile, for example, a shape between tubular and planar or a half cylindrical shape. One skilled in the art would understand that each of the distal and proximal anchoring portions of the device 100 may have other shapes as long as its intended anchoring function is fulfilled. According to various embodiments of the present teachings, the distal and proximal anchoring portions have a same profile. Alternatively, the distal and proximal anchoring portions may have different profiles. According to certain embodiments of the present teachings, the distal and proximal anchoring portions each has a general thickness of about 0.02 mm to about 1 mm.

Referring to FIG. 4, according to one embodiment 300 of the present teachings, the shunt portion 302 of the device 300 has a proximal end 312, a distal end 310, and a central lumen extending from the distal end 310 to the proximal end 312. The distal and anchoring portions 304 and 306 connect to the shunt portion 302 at its distal end 310 and proximal end 312, respectively. Upon deployment, the shunt portion 302 is positioned across an aperture between two heart chambers, with its distal end 310 and proximal end 312 positioned in two heart chambers on the opposite sides of the septum separating the two chambers. The shunt portion 302 functions as a conduit for fluid to flow from one end to the other. Thus, when the device 300 is deployed at the treatment site, the blood is allowed to flow from one heart chamber, through the shunt portion 302 of the device 300, to another heart chamber. FIG. 4 illustrates one embodiment of the present teachings where the shunt portion 302 of the deployed device 300 has a bent pre-set configuration with an overall curved length between about 3 mm and about 20 mm. According to one embodiment, the bent shunt portion 302 is straightened to align with the proximal and distal anchoring portions, 306, and 304 respectively, when the device 300 is delivered through a delivery system. One skilled in the art would understand that although FIG. 4 shows a bent shunt portion 302 upon deployment, the shunt portion 302 of the device 300 can have a relatively straight pre-set configuration in its delivery configuration, with an overall deployed length of about 3 mm to about 20 mm.

According to some embodiments, the shunt portion 302 of the device 300 as illustrated in FIG. 4 is stretched into an elongated profile with a longer axial length and a smaller cross section while the device 300 is being delivered; and upon deployment, the shunt portion 302 of the device 300 expands radially optionally with a shortened length.

Referring to FIG. 4, the distal and proximal anchoring portions 304 and 306 in this embodiment have a substantially planar profile. The distal anchoring portion 304 is attached to the distal end 310 of the shunt portion 302 and the proximal anchoring portion 306 attached to the proximal end of the shunt portion 302. According to some embodiments, in its delivery profile, the entire device 300 assumes a relatively straight profile with the distal anchoring portion 304, the proximal anchoring portion 306, and the shunt portion 302 approximately aligning with one another along an imaginary longitudinal axis. According to other embodiments, in its deployed profile, the device 300 assumes a hairpin or "U" shape profile, with the distal anchoring, portion 304 and the proximal anchoring portion 306 bending radially away from the longitudinal axis of device 300 at its delivery profile toward each other. Upon being deployed at the treatment location, the shunt portion 302 is positioned across an aperture between two heart chambers, the distal anchoring portion 304 disposed against the distal side of the septal wall, and the proximal anchoring portion 306 disposed against the proximal side of the septal wall.

Referring to FIGS. 1-4, in one embodiment of the present teachings, the ends of the distal and proximal anchoring portions are rounded to reduce stress against the septal tissue after the device is deployed. This round shape can easily be formed as part of the integral shape of the anchoring portions. In another embodiment of the present teachings, the distal and proximal anchoring portions have a greater flexibility than the shunt portion to allow the distal and proximal anchoring portions to conform to the anatomy of a heart with minimum stress concentrations imposed against the septal tissue. Alternatively, the free ends of the distal and proximal anchoring portions can have a greater flexibility than the rest of the anchoring portions. The increased flexibility can reduce stress concentrations against the septal tissue.

Referring to FIGS. 1-4, at least one of the distal and proximal anchoring portions and shunt portion is made of a biocompatible metal or polymer. In various embodiments, the entire device is made of a biocompatible metal or polymer. In some embodiments, the device in its entirely or the portion(s) with curved/bent deployment configuration is made of an elastic material, a super-elastic material, or a shape-memory alloy which allows the above portions to be distorted into a generally straightened profile during the delivery process and resume and maintain its intended profile in vivo once it is deployed from a delivery catheter. In some embodiments, the device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys, any other metallic alloys, or a mixture thereof. Alternatively, in such embodiments, a part of the device or the entire device is made of a polymer, such as PTFE, UHMPE, HDPE, polypropylene, polysulfone, or other biocompatible plastic. The surface finish of the device can be textured to induce tissue response and tissue in-growth for improved stabilization. Alternatively, a part of or all the device can be fabricated from a resorbable polymer such as polyactic acid, polyglycolic acid, polycaprolactone, a combination of two or more of the above or a variety of other resorbable polymers that are well known to those skilled in the art.

According to one embodiment of the present teachings, both the shunt portion and the two anchoring portions have an open mesh-like structure such that the device does not impede blood flow through the aperture even though the device resumes a curved deployed profile. According to one embodiment of the present teachings, each opening has a cross-sectional area of about 1 $mm^2$ to about 5 $mm^2$. According to another embodiment of the present teachings, the accumulated area of the openings in the mesh-like structure on the shunt portion of the device is about 50-95% of the entire cross section area of the shunt portion of the device and the accumulated area of the openings in the mesh-like structure is 50-95% of entire cross section area of the device.

In some embodiments of the present teachings, the device is fabricated by laser-cutting or acid-etching a pattern into a preformed tube, then shape-setting the device to the intended deployed configuration. In such embodiments, the mesh is formed by slotting a hollow tube, for example, with a machining laser, water drill, or other methods, and expanding the slotted hallow tube to form an open structure. Alternatively, the device may also be formed with a woven, knitted, or braided tubular metallic fabrics made out of metallic strands. The term "strand" used herein can be wires, cords, fibers, yarns, filaments, cables, threads, or the like, and these terms may be used interchangeably. According to one embodiment, the wire used to form the device has a general diameter from about 0.02 mm to about 1 mm. In another embodiment of the present teachings, the mesh is formed from wires that are pre-bent into the desired shape and then bonded together to connect elements either by welding or adhesively bonding. They can be welded by using a resistance welding technique or an arc welding technique, preferably in an inert gas environment and with cooling to control the grain structure in and around the weld site. These joints can be conditioned by using coining or upset forging to reduce the grain size and optimize the fatigue performance after the welding procedure.

According to one embodiment of the present teachings, the device is fabricated from a tube and then shaped to its final configuration. In one embodiment, if a sufficiently elastic and resilient material such as nitinol is used, the structure is preformed into the finished shape and then elastically deformed and stowed during the delivery so the device elastically recovers its shape upon deployment. In some embodiments, the shunt portions and/or distal and proximal portions are manually expanded to the desired diameter and/or curved to a pre-set shape and heat set in an oven while constrained to the desired shape.

In the embodiments where the distal and/or proximal anchoring portions of the device are less than a full cylinder, each of these portions can be formed by removing a part or most of the circumference of a tube from one end of the shunt portion to the free end of the tube, leaving the remaining part to be the anchoring portion. Alternatively, in the embodiments where the distal and/or proximal anchoring, portions of the device are less than a full cylinder, the shunt portion, the distal anchoring portion, and the proximal anchoring portion of the device are fabricated as individual components, which can then be connected to form the entire device.

According to one embodiment of the present teachings, at least one of the shunt portion and the two anchoring portions expands radially upon the device being deployed in vivo. According to one embodiment of the present teachings, upon deployment, the radial expansion of at least one of the shunt portion and the two anchoring portions is due to the elastic nature of the material. According to another embodiment of the present teachings, upon deployment, the radial expansion of at least one of the shunt portion and the two anchoring portions is due to its pre-set thermal shape memory of the material. According to yet another embodiment of the present teachings, upon deployment, the device is manually expanded radially via a balloon.

In the embodiments where the device is expanded in vivo via a balloon, the device can be mounted over a balloon catheter and the inflatable balloon is positioned inside the central lumen of the device. For example, the inflatable balloon can be positioned inside at least one of the shunt portion, the distal anchoring portion, and the proximal anchoring portion. In some embodiments, after the device is deployed at the treatment location, the balloon is then inflated and radially expands the shunt portion of the device. Then upon reaching a desired size, the balloon can then be deflated and retracted out of the device and back into the delivery catheter. According to another embodiment of the present teachings, the inflatable balloon is positioned inside the central lumen of the entire shunt portion, the distal and proximal anchoring portions of the device and all of the above portions of the device expand by inflating the balloon upon deployment. Alternatively, multiple inflatable balloons can be positioned in and inflate various portions of the device.

According to various embodiments of the present teachings, one or more radioopaque markers are used. Without attempting to limit to any particular function, these radioopaque markers can be visualized by using radiographic imaging equipments such as X-ray, magnetic resonance, ultrasound or other imaging techniques. Marker as disclosed herein can be applied to any part of a device or a delivery system of the present teachings. A radioopaque marker can be sewed, adhered, swaged riveted, otherwise placed, and secured in or on the device. The radioopaque marker may be made of tantalum, tungsten, platinum, irridium, gold, or alloys of these materials or other materials that are known to those skilled in the art. The radioopaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III), or other MR visible materials that are known to those skilled in the arts.

Figure 5:
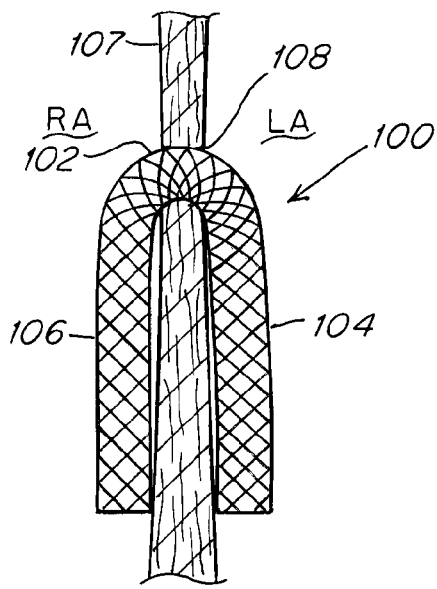
FIG. 5 is a perspective view of the exemplary pressure regulating device of FIG. 1 deployed at a target site between the left and right atria of a heart.

FIG. 5 depicts an embodiment of a pressure regulating device 100 of the present teachings, for example as illustrated in FIG. 1, deployed across the atrial septum 107. The distal anchoring portion 104 of the exemplary device 100 is disposed against the left atrial side of the septal tissue and the proximal anchoring portion 106 of the device 100 is disposed against the right atrial side of the septal tissue. The shunt portion 102 of the device 100 is positioned through the aperture 108 of the septum 107 to form a shunt. According to one embodiment of the present teachings, the two anchoring portions 104 and 106 of the device 100 apply a compression force against each side of the septal tissue so that the shunt portion 102 of the device 100 is held in the aperture 108.

According to one embodiment of the present teachings, as shown in FIG. 5, the distal anchoring portion 104 has a general uniform profile throughout the entire length. In this embodiment, the size and shape of the cross section of the distal anchoring portion 104 are generally consistent throughout the entire length of the portion. Similarly, in this particular embodiment, the proximal anchoring portion 106 has a uniform profile throughout the entire length of the portion. That is, the size and shape of the cross section of the proximal anchoring portion 106 are generally consistent throughout the entire length of the portion.

Figure 6:
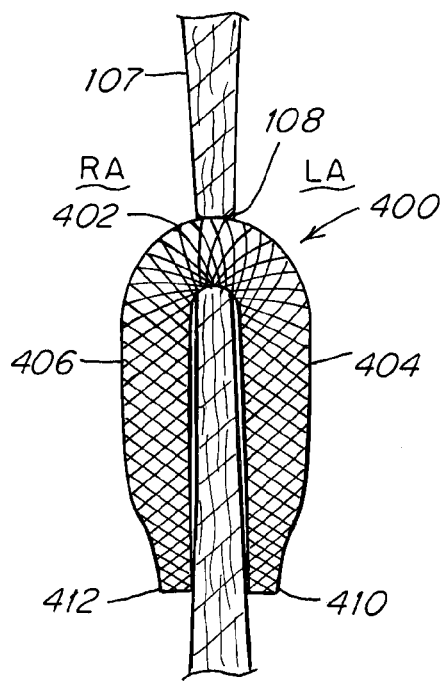
FIG. 6 is a side view of an exemplary pressure regulating device in accordance with the present teachings.
Figure 7:
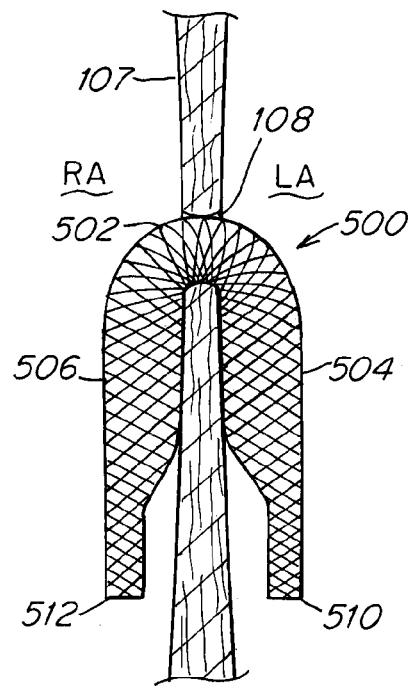
FIG. 7 is a side view of an exemplary pressure regulating device in accordance with the present teachings.

One skilled in the art would recognize that the size and shape of the cross section of the distal and proximal anchoring portions 104 and 106, can vary along the length of these portions. For example, as shown in FIGS. 6 and 7, each of the distal anchoring portions 404 and 504 of the device 400, 500 can have a stepped profile. According to this embodiment, each of the distal anchoring portions 404 and 504 has a cross section that is greater toward the shunt portions 402 and 502, respectively, than toward the free ends 410 and 510, respectively, with a cone-shaped transitional section between the cross sections towards the shunt portions 402 and 502, respectively, and the free ends 410 and 510, respectively. One skilled in art would recognize that although not shown in those figures, each of the distal anchoring portions 404 and 504 can also have a cone shape, gradually transitioning from a large cross section connecting to the shunt portions 402 and 502, respectively, to a small cross section at its free ends 410 and 510, respectively, of the device 400, 500. The reduced cross sections at the free ends of the distal anchoring portions can result in an increased flexibility of the free ends, which in some instances reduces stress concentration against the septum.

Continuing referring to FIGS. 6 and 7, in these embodiments, each of the proximal anchoring portions 406 and 506 of the device 400, 500, has a stepped profile. According to this embodiment, each of the proximal anchoring portions 406 and 506 has a large cross section toward the shunt portions 402 and 502, respectively, and a small cross section toward the free ends 412 and 512, respectively, with cone shaped transitional sections between the large cross section and small cross section of the proximal anchoring portions, 406, 506. One skilled in art would recognize that although not shown in the figures, each of the proximal anchoring portions 406 and 506 can also has a cone shape, gradually transitioning from a large cross section connecting to the shunt portions 402 and 502, respectively, to a small cross section at its free ends 412 and 512, respectively, of the device 400, 500. The reduced cross sections at the free ends of the proximal anchoring portions can result in an increased flexibility of the free ends, which in some instances reduces stress concentration against the septum.

Referring back to FIG. 6, upon deployment, the distal and proximal anchoring portions have a generally smooth/straight tubular surface lacing the septum 107 and a stepped tubular surface on the other side. This configuration provides two flexible free ends of the distal and proximal anchoring portions, 410 and 412, such that these two free ends can easily away from the septum 107 in order to accommodate the anatomy and reduce the risk of perforating the septal tissue. Alternatively, as shown in FIG. 7, upon deployment, the distal and proximal anchoring portions have a stepped tubular surface facing the septum 107 and a generally smooth tubular surface on the other side. In such embodiments, the free ends of the anchoring portions are designed to accommodate a thick septum.

It would be understood by those with ordinary skill in the art that each of the distal and proximal anchoring portions of the device can have a profile the same as or different from each other. Additionally, the distal and proximal anchoring portions can adopt other cross-section profile not illustrated in the figures throughout its length in order to conform to the anatomy of a septum.

The distal and proximal anchoring portions of the device can also have other features, for example, to secure the device at a treatment location. For example, referring to FIG. 8, the free end 610 of the distal anchoring portion 604 of the device 600 can have a distal tissue anchor 614 protruding toward the septum 107. Additionally, the free end 612 of the proximal anchoring portion 606 of the device 600 can have a proximal tissue anchor 616 protruding toward the septum 107. The distal and proximal tissue anchors 614 and 616 engage the septum 107 so that the device 600 can be held in place to reduce the risk of device embolization. Alternately, in some embodiments, not shown in FIG. 8, only one of the free ends 610 and 612 of the distal and proximal anchoring portions 604 and 606 of the device 600 has a tissue anchor. In some embodiments, the tissue anchor is located at the free end of the distal anchoring portion 604 of the device. In some embodiments, the tissue anchor is located at the free end of the proximal anchoring portion of the device. In another embodiment of the present teachings, the tissue anchor is positioned anywhere along the distal and/or proximal anchoring portions of the device. In yet another embodiment of the present teachings, the distal and/or proximal anchoring portions of the device has more than one tissue anchors. In another embodiment, only one of the distal and proximal anchoring portions has a tissue anchor(s). According to some embodiments, the distal and proximal tissue anchors are directly opposed to each other. According to some embodiments, the distal and proximal tissue anchors are not directly opposed to each other.

Figure 8:
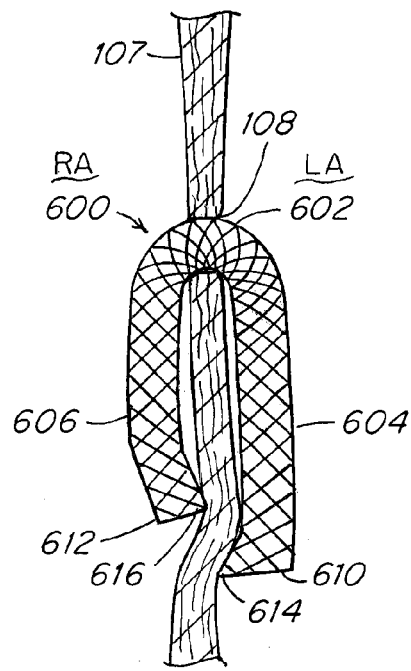
FIG. 8 is a side view of an exemplary pressure regulating device in accordance with the present teachings.

According to some embodiments of the present teachings, the distal anchoring portion and proximal anchoring portion have a same length. According to some embodiments, the distal anchoring portion has as different length from the proximal anchoring portion. FIG. 8 illustrates an exemplary embodiment where the distal and proximal anchoring portions have different lengths such that their free ends are not directly opposed to each other. As illustrated in FIG. 8, the distal anchoring portion 604 of the device 600 is longer than the proximal anchoring portion 606 of the device 600. Although not illustrated in the figures, one skilled in the art would recognize that the distal anchoring portion can have a shorter length than or the same length as the proximal anchoring portion.

In these particular embodiments, the distal tissue anchor 614 is at the free end 610 of the distal anchoring portion 604 and the proximal tissue anchor 616 is at the free end 612 of the proximal anchoring portion. 606. As the device 600 is positioned through an aperture on the septum 107, the tissue anchors 614 and 616 engage the septum 107 at the opposite sides to secure the device 600 at the aperture. Because the distal tissue anchor 614 and the proximal tissue anchor 616 are not directly opposite to each other, the configuration can reduce the relative movement of the device 600 against the septum 107, which in certain instances reduces the chance of device embolization and/or tissue abrasion against the device 600.

Figure 9:
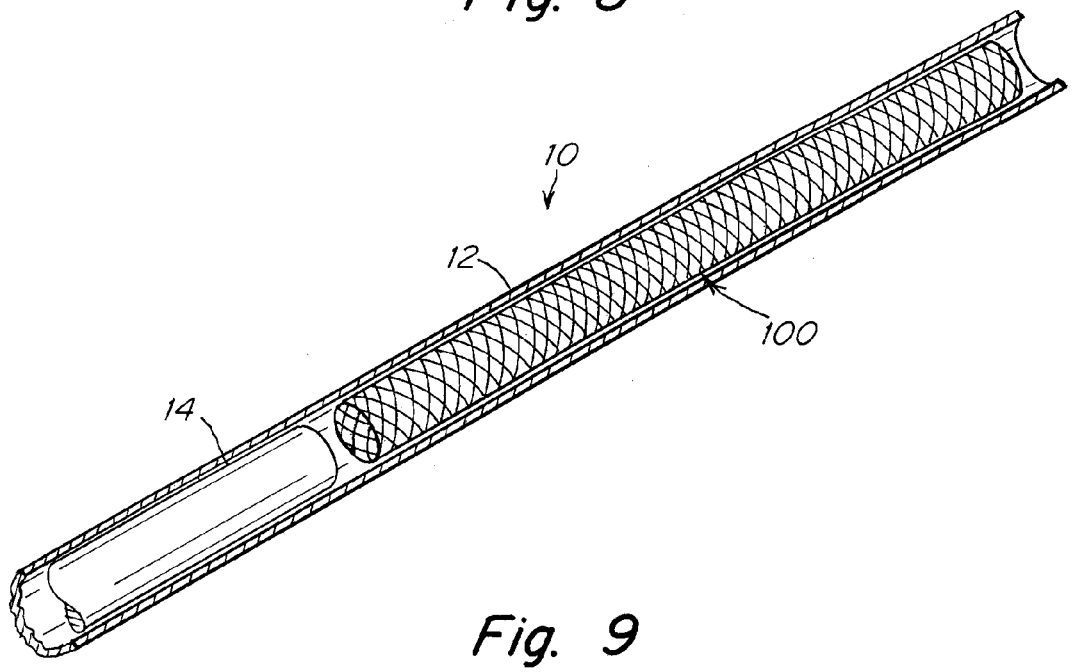
FIG. 9 is a side view of an exemplary delivery assembly in accordance with the present teachings.

FIG. 9 depicts an exemplary use of an embodiment of the present teachings in conjunction with a delivery system 10, which can be manipulated externally by a clinician. In this exemplary embodiment, the delivery system 10 includes a delivery sheath 12 with a distal end, a proximal end, an axial lumen, and a delivery catheter 14 slidably disposed within the lumen of the delivery sheath 12. Both the delivery sheath 12 and the delivery catheter 14 can be manipulated by a clinician at their proximal ends. As shown in FIG. 9, an device 100, extended into its elongated delivery profile, is slidably disposed within the distal portion of the delivery sheath 12 with the distal end of the elongated device 100 within the distal end of the delivery sheath 12, the proximal end of the elongated device 100 in contact with the distal end of the delivery catheter 14, and the distal end of the delivery catheter 14 designed to engage the proximal end of the elongated device 100 and push the device 101) distally outside of the delivery sheath 12 during a deployment. According to some embodiments, the delivery catheter is used to push the device 100 distally from the proximal end to the distal end of the delivery sheath or from the inside of the delivery sheath to outside of its distal end. The delivery catheter can also prevent the device 100 from sliding proximally during its delivery and deployment. Many engagement/attachment mechanisms known to those skilled in the art can be used between the delivery catheter 14 and the device 100 and what is illustrated in FIG. 9 is solely for illustration and should not be construed as limiting.

Figure 10:
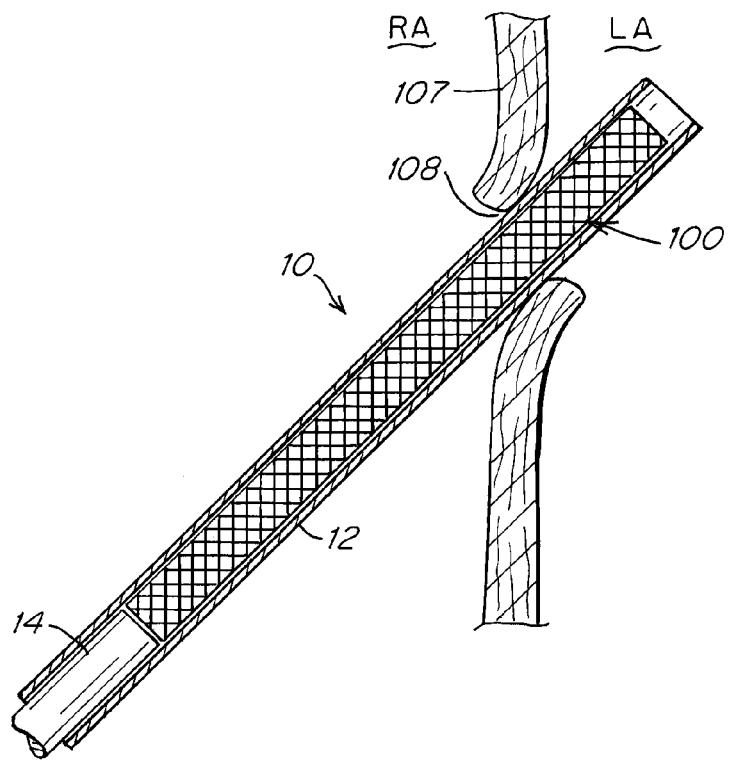
FIG. 10 illustrates an exemplary process in accordance with the present teachings where an exemplary delivery assembly is inserted to an exemplary insertion point.

FIGS. 10-13 depict exemplary steps for the deployment an exemplary pressure regulating device 100 inside a heart. Referring to FIG. 10, an aperture is located before the exemplary device 100 is introduced into the implantation site. In the event where no aperture exists in the septum, one can be created, for example, by puncturing the septum. Septal puncture procedures are well known to those with ordinary skill in the art. According to some embodiments, after an aperture is created, a guidewire, not shown, is placed across the aperture to guide the delivery and deployment of a device of the present teachings. Alternatively, the delivery assembly 10 can be used to deliver and deploy a device without the need of a guidewire.

In some embodiments, the delivery system 10 is inserted percutaneously by a clinician at an insertion point. As depicted in FIG. 10, the distal portion of the delivery assembly 10 is advanced percutaneously into the heart and toward the atrial septum 107. As shown in FIG. 10, the distal end of the delivery system 10, holding the device 100 in its elongated delivery profile, extends cross the aperture in the septum 107 and enter the left atrium, in some embodiments, a radio-opaque marker is used on the delivery sheath, the delivery catheter, or the device to aid a clinician in determining bow far the distal portion of the delivery assembly 10 extends inside the left atrium. According to some embodiments, the device is pre-loaded within the distal end of the delivery sheath and is carried across the atrial septum as the delivery sheath extends percutaneously. According to other embodiments, the delivery sheath is positioned across the septum first, the device is then pushed front the proximal end to the distal portion of the delivery sheath.

If the clinician is satisfied with the location, the clinician can start to deploy the device 100 by first deploying the distal half of the device 100 inside the left atrium. According to one embodiment, the delivery sheath 12 is retracted proximally with respect to the delivery catheter 14 to expose the distal half of the device 100. Alternatively, the deployment of the distal half of the device 100 can be accomplished by advancing the delivery catheter 14 distally with respect to the delivery sheath 12. As the delivery catheter 14 extends distally, the distal half of the device 100 is pushed outside of the distal end of the delivery sheath 12. As the distal half of the device 100 is exposed outside of the delivery sheath 12, the distal anchoring portion 104 of the device 100 bends radially away from the longitudinal axis of the elongated device or radially away from a longitudinal axis of the delivery system and assume its pre-set curved deployed configuration.

Figure 11:
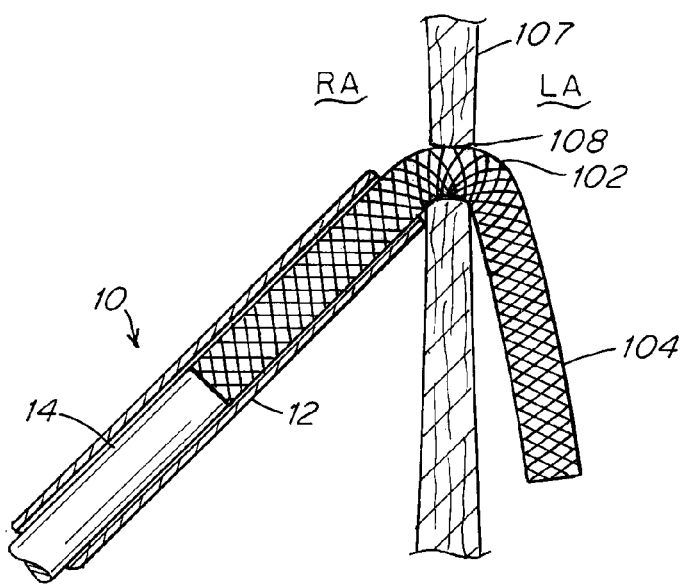
FIG. 11 illustrates an exemplary process in accordance with the present teachings where an exemplary pressure regulating device is partially deployed.

Referring to FIG. 11, the entire delivery assembly 10, including the delivery sheath 12, delivery catheter 14, and device 100 with its distal half deployed outside of the delivery system, and its proximal half still constrained inside the delivery system, is retracted proximally. As illustrated in FIG. 11, as the delivery system still holding the proximal half of the device 100, the distal half of the device 100 is positioned against the left atrial side of the septum 107 and the distal anchoring portion 104 of the device is pulled against the left atrial side of the septum 107.

Figure 12:
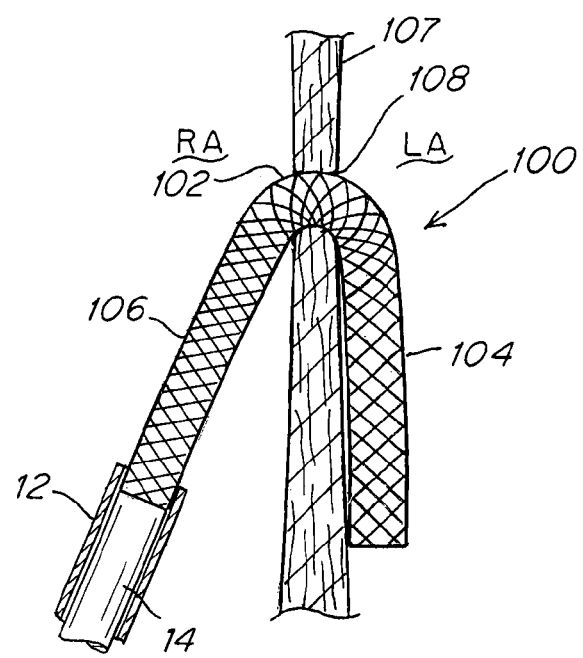
FIG. 12 illustrates an exemplary process in accordance with the present teachings where an exemplary pressure regulating device is partially deployed.

FIG. 12 illustrates the deployment of the proximal half of the exemplary device 100 using similar steps as described above. According to one embodiment, upon securing the distal anchoring portion 104 of the device 100 against the left atrial side of the septum 107, the delivery sheath 12 is then withdrawn proximally with respect to the delivery catheter 14 to expose the proximal half of the device 100 inside the right atrium. As the proximal half of the device 100 is exposed, the proximal anchoring portion 106 of the device 100 bends radially away from the longitudinal axis of the elongated device or radially away from a longitudinal axis of the delivery system and assume its pre-set curved deployed configuration.

According to one embodiment of the present teachings, during a deployment of the proximal half of the device 100, the free end of the proximal anchoring portion 106 of the device 100 remains inside the delivery sheath 12 such that the device 100 remains engaged with the delivery system 10. Alternatively, during the deployment of the proximal hall of the device 100, the free end of the proximal anchoring portion 106 of the device 100 exits the distal end of the delivery sheath 12, but remains engaged with the distal end of the delivery catheter 14 by means known to those skilled in the art. If the clinician is not satisfied with the deployment, the device can be retrieved. During retrieval, as the free end of the proximal anchoring portion 106 of the device 100 is held, the delivery sheath 12 is extended distally so that the distal portion of the sheath 12 slides over the proximal half of the device 100. Then the entire delivery assembly including the device 100, the sheath 12, and the catheter 14, extends distally into the left atrium. The delivery sheath 12 extends further distally as the free end of the proximal anchoring portion 106 of the device 100 is held steady so that the distal portion of the delivery sheath 12 slides over the distal half of the device 100. The entire delivery assembly can be retracted proximally and removed from the patient or the device can be redeployed by following the steps described herein. Although one retrieval method is described here, one skilled in the art would recognize that other retrieval methods can be incorporated without departing from the scope of the present teachings. For example, while the proximal end of the elongated device is engaged with the delivery assembly, a retrieval means can be advanced to retrieve the device.

Upon completing a deployment of the proximal half of the device 100, if the clinician is satisfied with the deployment, the device 100 can then be completely released, either by disengaging from the delivery catheter 14 or by pushing the device 100 completely outside of the delivery sheath 12. The delivery sheath 12 and the delivery catheter 14 can then be withdrawn outside of the body.

Figure 13:
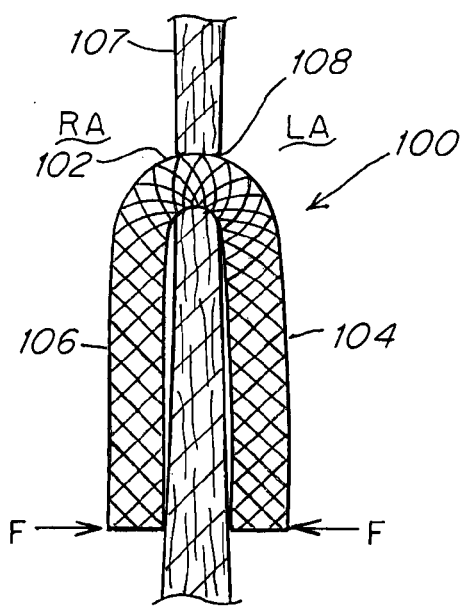
FIG. 13 illustrates an exemplary process in accordance with the present teachings where an exemplary pressure regulating device is deployed.

An exemplary device 100 in its fully deployed configuration is depicted in FIG. 13. When fully deployed, the device 100 rests across the aperture with the distal anchoring portion 104 and the proximal anchoring portion 106 exerting a compressive force F against a septum 107 from the opposite sides of the septum 107 to secure the shunt portion 102 of the device 100 in the aperture.

The techniques disclosed for deploying the embodiments described herein are solely for illustration. It should be understood that other techniques can be used instead of, or in combination with, these disclosure, especially because a clinician can select a technique to deploy an embodiment or the devices described herein based on the particular features of the device, the delivery system, and the anatomy in which the device is being deployed.

One skilled in the art would recognize that a device of the present teachings may be used in combination with one or more tissue scaffolds, one or more medications, one or more growth factors, other agents, or any combination thereof, for example, to control tissue in-growth at the aperture. The tissue scaffold can be made of any flexible, biocompatible material capable of controlling host tissue growth including, but not limited to, polyester fabrics, Teflon-based materials, such as ePTFE, polyurethanes, metallic materials, polyvinyl alcohol (PVA), extracellular matrix (ECM) isolated from a mammalian tissue, or other bioengineered materials, bioabsorbable polymers, or other natural materials (e.g., collagen), or combinations of these materials. Furthermore, the surface of the tissue scaffold can be modified with biological, pharmaceutical and/or other active ingredients, such as anti-coagulants, anti-thrombogenic agents, cells, growth factors and/ or drugs to diminish calcifications, protein deposition, and thrombus, which control and direct tissue growth by stimulating an irritation response to induce cell proliferation in one area and discourage cell proliferation in the other. A tissue scaffold can be attached to the entire device or the shunt portion of the device alone by sutures, heat treatment, adhesives, or any other bonding process. One skilled in the art would also recognize that a device of the present teachings can be adjusted according to the pressure difference between the heart chambers.

In various embodiments, each of the drugs, growth factors, and/or other agents referred herein is selected from an adenovirus with or without genetic material, angiogenic agents, angiotensin converting enzyme inhibitors (ACE inhibitors), angiotensin II antagonists, anti-angiogenic agents, antiarrhythmics, anti-bacterial agents, antibiotics (including Erythromycin, Penicillin), anti-coagulants (including Heparin), anti-growth factors, anti-inflammatory agents (including Dexamethasone, Aspirin, Hydrocortisone), antioxidants, anti-platelet agents, Forskolin, anti-proliferation agents, anti-rejection agents, Rapamycin, anti-restenosis agents, anti-sense, anti-thrombogenic agents, argatroban Hirudin, GP IIb/ IIIa inhibitors, antivirus drugs, arteriogenesis agents, acidic fibroblast growth factor (aFGF), angiogenin, angiotropin, basic fibroblast growth factor (bFGF), Bone morphogenic proteins (BMP), epidermal growth factor (EGF), fibrin, granulocyte-macrophage colony stimulating factor (GM-CSF), hepatocyte growth factor (HGF), HIF-1, insulin growth factor-1 (IGF-1), interleukin-8 (IL-8), MAC-I; nicotinamide platelet-derived endothelial cell growth factor (PD-ECGF), platelet-derived growth factor (PDGF), transforming growth factors alpha & beta (TGF-a, TGP-b), tumor necrosis factor alpha (TNF-a), vascular endothelial growth factor (VEGF), vascular permeability factor (VPF), bacteria beta blocker, blood clotting factor, calcium channel blockers, carcinogens, cells, bone marrow cells, blood cells, stem cells, umbilical cord cells, fat cells, chemotherapeutic agents (e.g., Ceramide, Taxol, Cisplatin), cholesterol reducers, chondroitin collagen inhibitors, colony stimulating factor, coumadin, cytokines, prostaglandins, dentin etretinate genetic material, glucosamine, glycosaminoglycans, L-703, 081, growth factor antagonists or inhibitors, growth factors, autologous growth Factors, basic fibroblast growth factor (bFGF), bovine derived growth factors, cartilage derived growth factors (CDF), endothelial cell growth factor (ECGF), fibroblast growth factors (FGF), nerve growth factor (NGF), recombinant NGF (rhNGF), recombinant growth factors, tissue derived cytokines, tissue necrosis factor (TNF), growth hormones, heparin sulfate proteoglycan, HMC-CoA reductase inhibitors (statins), hormones, erythropoietin, immoxidal, immunosuppressant agents, inflammatory mediator, insulin, interleukins, lipid lowering agents, lipo-proteins, low-molecular weight heparin, lymphocytes, lysine, morphogens nitric oxide (NO), nucleotides, peptides, PR39, proteins, prostaglandins, proteoglycans, perlecan radioactive materials, iodine-125, iodine-131, iridium-192, palladium 103, radiopharmaceuticals, secondary messengers, ceramide, somatomedins, statins, steroids, sulfonyl thrombin, thrombin inhibitor, thrombolytics, ticlid, tyrosine kinase, inhibitors, ST638, AG17, vasodilator, histamine, nitroglycerin, vitamins E and C, yeast. Certain embodiments of the present teachings could also be modified so as to deliver one or more alarmin(s) or alarmin activator(s), or a combination of alarmin(s) and alarmin activator(s) to the intracardiac tissue to accelerate recruitment of endogenous cells, for example, fibroblasts, myocytes, endothelial cells and their progenitors, and progenitor cells of the circulating blood, formation of granulation tissue and re-endothelialization at the site of the intracardiac defect. Exemplary alarmins include members of the family of damage associated molecular pattern molecules (DAMPs) and members of the family of pathogen associated molecular pattern molecules (PAMPs). Exemplary alarmins further include the nuclear protein HMGB1, the S100 family of molecules (cytosolic calcium-binding proteins), heat shock proteins, interleukins (including IL-1a), HDGF (hepatoma-derived growth factor, Gal1 (Galectin 1) and the purinergic metabolites of ATP, AMP, adenosine and uric acid. Alarmin activators include small molecules that are necessary for maintaining the activity of administered and/or endogenous alarmins. Exemplary alarmin activators include thiol containing reducing agents, including, but not limited to, dithiothreitol, 2-mercaptoethanol, N-7-acetyl-cysteine, sodium sulfite, glutathione, and Probucol® (2,6-ditert-butyl-4-[2-(3,5-ditertbutyl-4-hydroxyphenyl)sulfanylpropan-2-yl-sulfanyl]phenol). Exemplary alarmin activators further include non-thiol reducing agents, including, but not limited to, ascorbic acid, sodium hypophosphite, and sodium borohydride.

The methods and devices disclosed above are useful for treating the symptoms of heart failures, in particular diastolic heart failures, by reducing the pressure in the left atrium and pulmonary veins. One skilled in the art would further recognize that devices according to the present teachings could be used to regulate pressure in other parts of the heart and/or vascular portions of the body. For example, the devices disclosed herein can be deployed on the septum between the left and right atria, the left and right ventricles, left atrium and coronary sinuses, and the like.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

I claim:

1. A device comprising:
   a shunt portion comprising a distal end, a proximal end, and a central lumen,
   a distal anchoring portion connecting to the distal end of the shunt portion, and
   a proximal anchoring portion connecting to the proximal end of the shunt portion,
   wherein the device has a first configuration where the shunt portion, the distal anchoring portion, and the proximal anchoring portion approximately align along a longitudinal axis, and
   the device has a second configuration where the distal anchoring portion and the proximal anchoring portion turn radially away from the longitudinal axis and the device assumes a general "U" shape.

2. The device of claim 1, wherein the distal anchoring portion, the proximal anchoring portion, and the shunt portion form an elongated tube in the first configuration.

3. The device of claim 1, wherein the distal anchoring portion, the proximal anchoring portion, and the shunt portion form an U shaped tube in the second configuration.

4. The device of claim 3, wherein the distal anchoring portion, the proximal anchoring portion, and the shunt portion each comprises a tubular surface with a plurality of openings.

5. The device of claim 1, wherein the shunt portion further comprises a tubular surface with a plurality of openings.

6. The device of claim 1, wherein the shunt portion has a first cross-sectional size when the device is in the first configuration, and a second cross-sectional size when the device is in the second configuration, wherein the first cross-sectional size is smaller than the second cross-sectional size.

7. The device of claim 1, wherein the device is adapted to be positioned across an aperture in the heart in its second configuration with the distal anchoring portion contacting one side of the aperture, the proximal anchoring portion contacting the other side of the aperture, and the shunt portion positioned across the aperture.

8. The device of claim 7, wherein the device is adapted to allow blood to flow from one side of the aperture through the central lumen of the shunt portion to the other side of the aperture.

9. The device of claim 1 comprising at least one tissue anchor on at least one of the distal anchoring portion and the proximal anchoring portion.

10. The device of claim 1, wherein the distal and proximal anchoring portions each has a generally tubular profile.

11. The device of claim 1, wherein the distal and proximal anchoring portions each has a half cylindrical profile.

12. The device of claim 1, wherein at least one of the distal and proximal anchoring portions is more flexible than the shunt portion.

13. A delivery assembly comprising:
   a delivery sheath comprising a distal portion and a lumen,
   a delivery catheter comprising a distal end,
   wherein the delivery catheter is disposed within the lumen of the distal portion of the delivery sheath, and
   a device disposed within the lumen of the distal portion of the delivery sheath,
   wherein the device comprises a shunt portion, a distal anchoring portion, and a proximal anchoring portion,
   wherein the shunt portion comprising a distal end, a proximal end, and a central lumen; the distal anchoring portion is connected to the distal end of the shunt portion; the proximal anchoring portion is connected to the proximal end of the shunt portion; the device has a first configuration where the shunt portion, the distal anchoring portion, and the proximal anchoring portion of the device approximately align with a longitudinal axis; and the device has a second configuration where the distal anchoring portion and the proximal anchoring portion turn radially away from the longitudinal axis and the device assumes a general "U" shape; and
   the distal end of the delivery catheter engages the proximal anchoring portion of the device.

14. The delivery assembly of claim 13, wherein the shunt portion further comprises to tubular surface with a plurality of openings.

15. The delivery assembly of claim 13, wherein the shunt portion has a first cross-sectional size when the device is in the first configuration and a second cross-sectional size when the device is in the second configuration, wherein the first cross-sectional size is smaller than the second cross-sectional size.

16. The delivery assembly of claim 13, wherein the device is adapted to be positioned across an aperture in the heart in its second configuration with the distal anchoring portion contacting one side of the aperture, the proximal anchoring portion contacting the other side of the aperture, and the shunt portion positioned across the aperture.

17. The delivery assembly of claim 13, wherein at least one of the distal and proximal anchoring portions of the device is more flexible than the shunt portion.

18. A method of implanting a device between the left and right atria of a heart comprising:
  providing a delivery assembly comprising a delivery system comprising a lumen and a device disposed within the lumen of the delivery system,
  wherein the device comprises a shunt portion, a distal anchoring portion, and to proximal anchoring portion,
  wherein the shunt portion comprising a distal end, a proximal end, and a central lumen; the distal anchoring portion is connected to the distal end of the shunt portion; the proximal anchoring portion is connected to the proximal end of the shunt portion; the device has a first configuration where the shunt portion, the distal anchoring portion, and the proximal anchoring portion of the device approximately align with a longitudinal axis; and the device has a second configuration where the distal anchoring portion and the proximal anchoring portion turn radially away from the longitudinal axis and the device assumes a general "U" shape; and
  advancing the delivery assembly through an aperture in the septum between the left and right atria of a heart, exposing the distal anchoring portion of the device so that the distal anchoring portion of the device turns radially away from the longitudinal axis,
  retracting the delivery assembly proximally so that the distal anchoring portion of the device contacts the left atrial side of the septum,
  exposing the proximal anchoring portion of the device so that the distal anchoring portion of the device turn radially away from the longitudinal axis,
  retracting the delivery system from the body, leaving the device positioned across the aperture in its second configuration with the distal anchoring portion contacting the left atrial side of the septum, the proximal anchoring portion contacting the right atrial side of the septum, and the shunt portion positioned across the aperture.

19. The method of claim 18, wherein the delivery system comprises a delivery catheter engaging the proximal anchoring portion of the device.

* * * * *